(12) United States Patent
Dresher et al.

(10) Patent No.: US 10,743,920 B2
(45) Date of Patent: Aug. 18, 2020

(54) BONE COMPRESSION PLATE

(71) Applicant: ARTHREX, Inc., Naples, FL (US)

(72) Inventors: Brad Dresher, Colorado Springs, CO (US); Mihaela Morar, Fort Myers, FL (US); Chris Powell, Naples, FL (US); Michael J. Dresher, Wichita, KS (US)

(73) Assignee: ARTHREX, INC., Naples, FL (US)

( * ) Notice: Subject to any disclaimer, the term of this patent is extended or adjusted under 35 U.S.C. 154(b) by 618 days.

(21) Appl. No.: 15/372,861

(22) Filed: Dec. 8, 2016

(65) Prior Publication Data
US 2017/0156768 A1    Jun. 8, 2017

Related U.S. Application Data

(60) Provisional application No. 62/264,390, filed on Dec. 8, 2015.

(51) Int. Cl.
*A61B 17/80*    (2006.01)
*A61B 17/86*    (2006.01)
*A61B 90/00*    (2016.01)

(52) U.S. Cl.
CPC ...... *A61B 17/8019* (2013.01); *A61B 17/8009* (2013.01); *A61B 17/8057* (2013.01); *A61B 17/86* (2013.01); *A61B 17/8605* (2013.01); *A61B 2090/033* (2016.02); *A61B 2090/0807* (2016.02)

(58) Field of Classification Search
CPC . A61B 17/86; A61B 17/8605; A61B 17/8057; A61B 17/8009; A61B 17/8019; A61B 17/80; A61B 17/8004; A61B 17/8014; A61B 17/8052; A61B 2090/033; A61B 2090/0807

USPC .......... 600/70–71, 280–299; 606/70–71, 606/280–299
See application file for complete search history.

(56) References Cited

U.S. PATENT DOCUMENTS

| | | | | |
|---|---|---|---|---|
| 3,552,389 A | * | 1/1971 | Allgower | A61B 17/8014 606/282 |
| 3,604,414 A | * | 9/1971 | Borges | A61B 17/8009 606/105 |
| 3,659,595 A | * | 5/1972 | Haboush | A61B 17/8009 606/71 |
| 4,119,092 A | * | 10/1978 | Gil | A61B 17/8004 606/96 |
| 6,533,786 B1 | * | 3/2003 | Needham | A61B 17/1728 606/282 |
| 8,685,067 B2 | | 4/2014 | King et al. | |
| 8,740,915 B2 | | 6/2014 | Niederberger et al. | |
| 8,758,347 B2 | * | 6/2014 | Weiner | A61B 17/8009 606/71 |

(Continued)

*Primary Examiner* — Jessica Weiss
(74) *Attorney, Agent, or Firm* — Carlson, Gaskey & Olds

(57) ABSTRACT

A bone plate according to an exemplary aspect of the present disclosure includes, inter alia, a body portion. The body portion includes a first slotted portion extending at least partially through the body portion and a plurality of teeth adjacent the first slotted portion for engaging a driver in the first slotted portion. The body portion also includes a second slotted portion extending at least partially through the body portion and a ramped portion at least partially surrounding the second slotted portion. The ramped portion tapers from an outer surface of the body portion toward an inner surface of the body portion.

19 Claims, 12 Drawing Sheets

(56) References Cited

U.S. PATENT DOCUMENTS

| | | |
|---|---|---|
| 8,936,615 B2 | 1/2015 | Pappalardo et al. |
| 9,138,270 B2 | 9/2015 | Lazoglu et al. |
| 2005/0096657 A1* | 5/2005 | Autericque ........ A61B 17/7059 623/17.11 |
| 2009/0171399 A1* | 7/2009 | White .................... A61B 17/80 606/286 |
| 2009/0234359 A1 | 9/2009 | Onoue et al. |
| 2009/0264934 A1 | 10/2009 | Youssef et al. |
| 2011/0098757 A1 | 4/2011 | Schelling |
| 2011/0224736 A1* | 9/2011 | Humphrey ......... A61B 17/1728 606/289 |
| 2011/0264149 A1* | 10/2011 | Pappalardo ........ A61B 17/8019 606/286 |
| 2011/0288595 A1* | 11/2011 | Niederberger ..... A61B 17/8019 606/286 |
| 2011/0319939 A1 | 12/2011 | Kretzer et al. |
| 2012/0197303 A1* | 8/2012 | King .................. A61B 17/1728 606/282 |
| 2013/0253592 A1 | 9/2013 | Larche et al. |
| 2015/0230838 A1* | 8/2015 | Lazoglu ............. A61B 17/8009 606/71 |
| 2015/0230841 A1* | 8/2015 | Freese ............... A61B 17/8052 606/279 |

\* cited by examiner

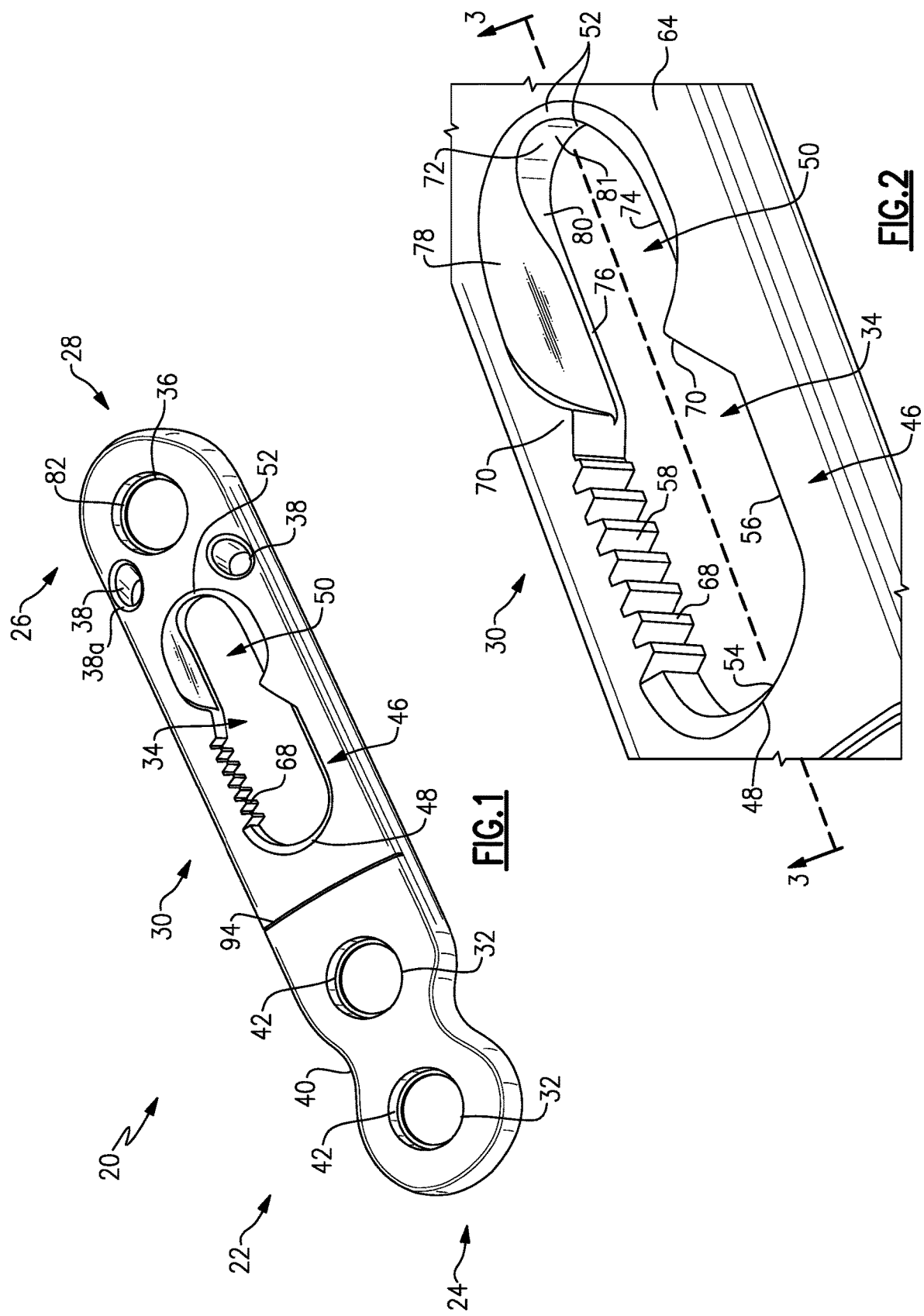

BONE COMPRESSION PLATE

CROSS-REFERENCE TO RELATED APPLICATIONS

This application claims priority to U.S. Provisional Application No. 62/264,390, which was filed on Dec. 8, 2015.

BACKGROUND

This disclosure relates to a surgical device and method of using the surgical device to attach adjacent pieces of bone. More particularly, this disclosure is directed to a compression plate used to compress adjacent bones or pieces of a bone together.

Orthopedic procedures are often performed to repair skeletal injuries. For example, a bone may develop a complete or partial fracture from a sports injury or accident. When such fractures occur, the separated pieces of bone must be brought back together to facilitate healing and stability. Bone compression plates are one type of surgical device developed to facilitate these repairs. Additionally, bones may be fused together in a fusion process.

SUMMARY

This disclosure describes various bone plate assemblies, such as compression plates, and associated surgical techniques for attaching adjacent bones together and/or fixing adjacent bones relative to each other. Compression plates can be made of a metallic or a composite material that is biocompatible. The compression plates include an elongated slot including teeth configured to engage complementary teeth on a tool to compress the adjacent bones together during fixation.

A bone plate according to an exemplary aspect of the present disclosure includes, inter alia, a body portion. The body portion includes a first slotted portion extending at least partially through the body portion and a plurality of teeth adjacent the first slotted portion for engaging a driver in the first slotted portion. The body portion also includes a second slotted portion extending at least partially through the body portion and a ramped portion at least partially surrounding the second slotted portion. The ramped portion tapers from an outer surface of the body portion toward an inner surface of the body portion.

A bone plate assembly according to an exemplary aspect of this disclosure includes, inter alia, a body portion and a driver. The body portion includes a first slotted portion extending at least partially through the body portion and a first plurality of teeth are located adjacent a first side of the first slotted portion for engaging a driver in the first slotted portion. A second plurality of teeth are located adjacent a second side of the first slotted portion for engaging a driver in the first slotted portion.

A surgical method according to an exemplary aspect of this disclosure includes, inter alia, attaching a bone plate having a body portion to a first bone segment. A second bone segment is engaged with a compression tool in a first slotted portion of the body portion for bringing the first bone segment towards the second bone segment. The first bone segment is compressed against the second bone segment by engaging a fastener against a ramped portion on the compression plate.

BRIEF DESCRIPTION OF THE DRAWINGS

FIG. 1 illustrates a compression plate according to a first embodiment of this disclosure.

FIG. 2 illustrates an enlarged view of a portion of the compression plate shown in FIG. 1.

DETAILED DESCRIPTION

Figure 3:
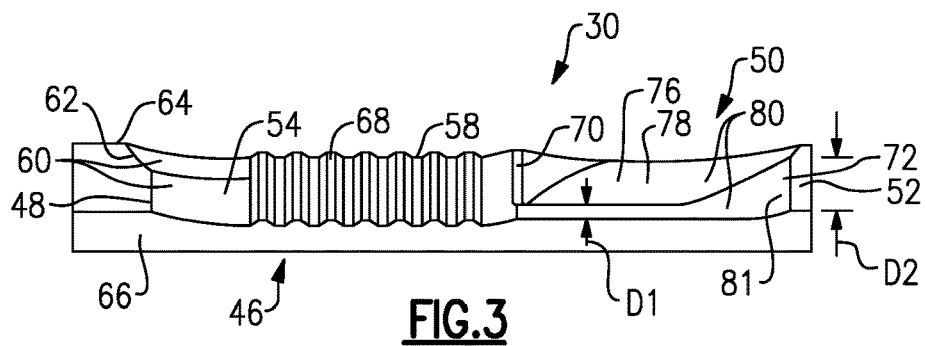
FIG. 3 is a cross-sectional view taken along line 3-3 of FIG. 2.

This disclosure describes various bone plate assemblies, such as compression plates, and associated surgical techniques for attaching adjacent bones together and/or fixing adjacent bones relative to each other. Compression plates can be made of a metallic or a composite material that is biocompatible. The compression plates include an elongated slot including teeth configured to engage complementary teeth on a tool to compress the adjacent bones together during fixation.

A bone plate according to an exemplary aspect of the present disclosure includes, inter alia, a body portion. The body portion includes a first slotted portion extending at least partially through the body portion and a plurality of teeth adjacent the first slotted portion for engaging a driver in the first slotted portion. The body portion also includes a second slotted portion extending at least partially through the body portion and a ramped portion at least partially surrounding the second slotted portion. The ramped portion tapers from an outer surface of the body portion toward an inner surface of the body portion.

In a further embodiment, a body portion includes a first end and a second end. A first end includes at least one fastener opening for attaching the body portion to a first bone segment and a second slotted portion is configured to align with a second bone segment separate from a first bone segment.

In a further embodiment, a second slotted portion includes a wall including a ramped portion and a surface portion.

In a further embodiment, a surface portion includes a first dimension between an inner surface of the body portion and a ramped portion along a first side of a second slotted portion. A surface portion includes a second dimension at a second end of a second slotted portion.

In a further embodiment, an intersection between a ramped portion and a surface portion tapers in a direction from a second end of a second slotted portion to a first end of a second slotted portion.

In a further embodiment, a first end of second slotted portion is configured to be closer to a first bone segment than a second end of a second slotted portion.

In a further embodiment, a first plurality of teeth are located on a first side of a first slotted portion. A second plurality of teeth are located on a second side of a first slotted portion.

In a further embodiment, a first slotted portion includes a threaded fastener opening which includes a sidewall extending less than 360 degrees.

In a further embodiment, a body portion is a single piece unitary component.

A bone plate assembly according to an exemplary aspect of this disclosure includes, inter alia, a body portion and a driver. The body portion includes a first slotted portion extending at least partially through the body portion and a first plurality of teeth are located adjacent a first side of the first slotted portion for engaging a driver in the first slotted portion. A second plurality of teeth are located adjacent a second side of the first slotted portion for engaging a driver in the first slotted portion.

In a further embodiment, a first plurality of teeth include a first coarseness and a second plurality of teeth include a second coarseness different from a first coarseness and the second plurality of teeth engage a locking portion of a driver.

In a further embodiment, a second slotted portion extends at least partially through a body portion and a ramped portion at least partially surrounding a second slotted portion. A ramped portion tapers from an outer surface of a body portion toward an inner surface of a body portion.

In a further embodiment, a second slotted portion includes a wall that has a ramped portion and a surface portion. A surface portion includes a first dimension between an inner surface of a body portion and a ramped portion along a first side of a second slotted portion. A surface portion includes a second dimension at a second end of a second slotted portion.

In a further embodiment, an intersection between a ramped portion and a surface portion tapers in a direction from a second end of a second slotted portion to a first end of a second slotted portion.

A surgical method according to an exemplary aspect of this disclosure includes, inter alia, attaching a bone plate having a body portion to a first bone segment. A second bone segment is engaged with a compression tool in a first slotted portion of the body portion for bringing the first bone segment towards the second bone segment. The first bone segment is compressed against the second bone segment by engaging a fastener against a ramped portion on the compression plate.

In a further embodiment, a step of compressing the first bone segment against a second bone segment includes locating the fastener in a second slotted portion extending at least partially through a body portion. A ramped portion at least partially surrounds a second slotted portion.

In a further embodiment, a second slotted portion includes a wall that has a ramped portion and a surface portion. A surface portion includes a first dimension between an inner surface of a body portion and a ramped portion along a first side of a second slotted portion. A surface portion includes a second dimension at a second end of a second slotted portion.

In a further embodiment, an intersection between a ramped portion and a surface portion tapers in a direction from a second end of a second slotted portion to a first end of a second slotted portion.

In a further embodiment, a first plurality of teeth is engaged on a first side of a first slotted portion with a compression tool. A second plurality of teeth is engaged on a second side of a first slotted portion with a compression tool.

In a further embodiment, a second plurality of teeth contribute to bringing a first bone segment towards a second bone segment when a compression tool is rotated in a first direction and a first plurality of teeth contribute to preventing a compression tool from rotating in a second direction.

FIG. 1 illustrates a compression plate 20 according to a first non-limiting embodiment. The compression plate 20 is elongated and includes a first portion 22 adjacent a first end 24, a second portion 26 adjacent a second end 28, and a mid-portion 30 between the first portion 22 and the second portion 26 forming a single unitary piece. A body portion of the compression plate 20 may be formed from a combination of the first portion 22, second portion 26, and third portion 30. The first portion 22 includes at least one fastener opening 32, the mid-portion 30 includes an elongated slot 34, and the second portion 26 includes at least one fastener opening 36 and at least one tack opening 38. In a non-limiting embodiment, the compression plate 20 includes a longitudinal axis extending through the first end 24 and the second end 28 that is generally parallel to a length of the elongated slot 34. In another non-limiting embodiment, the compression plate 20 could include a square, elliptical, triangular, or other shape suitable to join adjacent segments of bone. The size of the compression plate 20 can also vary depending on application and patient size.

In the illustrated non-limiting embodiment, the fastener openings 32 in the first portion 22 are spaced longitudinally along the compression plate 20. The first portion 22 can include a neck 40 of reduced width between each of the fastener openings 32 or between an adjacent pair of fastener openings 32. In a non-limiting embodiment, each of the fastener openings 32 include internal threads 42 that engage fasteners 96 (see FIG. 5) to secure the fasteners 96 to the compression plate 20. In another non-limiting embodiment, each of the fastener opening 32 are defined by a smooth internal surface. In the illustrated non-limiting embodiment, the at least one fastener opening 32 includes a pair fastener openings 32 spaced longitudinally along the compression plate 20. In another non-limiting embodiment, the fastener openings 32 could be offset from each other relative to the longitudinal axis of the compression plate 20.

FIGS. 1-3 illustrate the mid-portion 30 of the compression plate 20. In the illustrated non-limiting embodiment, the elongated slot 34 includes a first slotted portion 46 adjacent a first end 48 and a second slotted portion 50 adjacent a second end 52. The first end 48 of the elongated slot 34 is located closer to the first end 24 of the compression plate 20 than the second end 52 of the elongated slot 34 and the second end 52 of the elongated slot 34 is located closer the second end 28 of the compression plate 20 than the first end 48 of the elongated slot 34. However, the location of the first end 48 and the second end 52 of the elongated slot 34 can vary in relation to the first end 24 and the second end 28 of the compression plate 20. In a non-limiting embodiment, the first slotted portion 46 is connected to the second slotted portion 50 via an open portion. In another non-limiting embodiment, the first slotted portion 46 is separated from the second slotted portion 50 such that the first slotted portion 46 and the second slotted portion 50 form two separate and distinct slots.

The first slotted portion 46 of the elongated slot 34 includes a first rounded portion 54 connecting a first side 56 of the elongated slot 34 to a second side 58 of the elongated slot 34. The first rounded portion 54, the first side 56, and the second side 58 include a wall 60 having a chamfered portion 62. The wall 60 extends between an inner surface 66 of the compression plate and an outer surface 64 of the compression plate. The chamfered portion 62 is located adjacent the outer surface 64 of the compression plate 20 such that an edge of the chamfered portion 62 intersects the outer surface 64.

The second side 58 of the first slotted portion 46 includes a plurality of teeth 68 extending between the inner surface 66 and the outer surface 64. In another non-limiting embodiment, the teeth 68 extend only a portion of the distance between the inner surface 66 and the outer surface 64. The teeth 68 extend along the second side 58 from the first rounded portion 54 to a transition portion 70. The transition portion 70 separates the first slotted portion 46 from the second slotted portion 50 while maintaining continuity of the elongated slot 34 between the first slotted portion 46 and the second slotted portion 50.

The second slotted portion 50 of the elongated slot 34 includes a second rounded portion 72 connecting a first side 74 of the second slotted portion 50 with a second side 76 of the second slotted portion 50. The first and second sides 74, 76 and the second rounded portion 72 form a wall 80. The wall 80 includes a surface portion 81 and a ramped portion 78, such as a chamfer or another transition surface. The surface portion 81 extends from the inner surface 66 and intersects the ramped portion 78 along an edge of the ramped portion 78. The intersection between the ramped portion 78 and the surface portion 81 tapers toward the inner surface 66 from the second rounded portion 72 towards the transition portion 70. The ramped portion 78 also forms a contact surface for engaging a screw head to provide compression between separated bones as discussed further below.

The surface portion 81 extending along the first and second sides 74, 76 includes a first dimension D1 extending between the inner surface 66 and the intersection of the surface portion 81 and the ramped portion 78. The surface portion 81 adjacent the second end 52 includes a second dimension D2 extending between the inner surface 66 and the intersection of the surface portion 81 and the ramped portion 78. The first and second dimensions D1 and D2 extend perpendicular to at least one of the inner and outer surfaces 66, 64. In the illustrated non-limiting embodiment, the second dimension D2 is greater than the first dimension D1 and the first dimension D1 along the first and second sides 74, 76 decreases as it moves further away from the second end 52. The variation in the first and second dimensions D1, D2 creates the tapering of the ramped portion 78. In a non-limiting embodiment, the dimension D2 is at least three (3) times the dimension D1. In another non-limiting embodiment, the dimension D2 is at least two (2) times the dimension D1.

Figure 12:
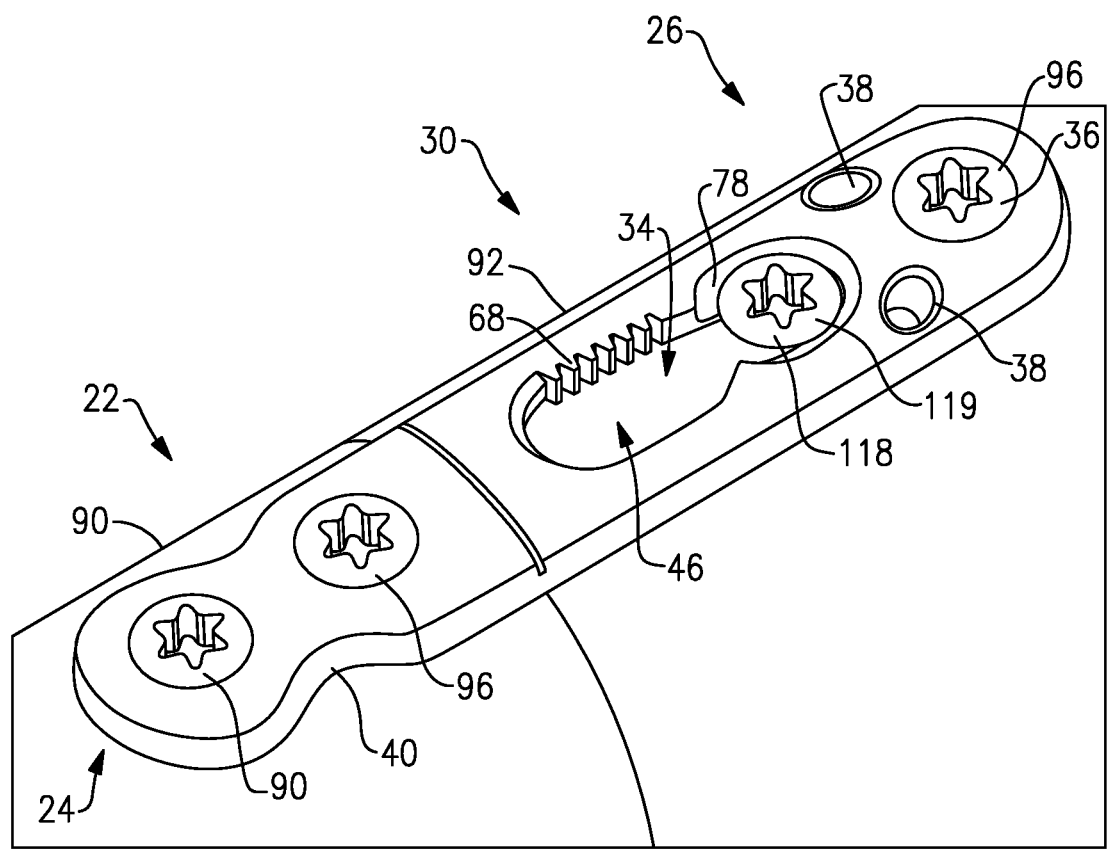

The second portion 26 of the compression plate 20 includes the at least one fastener opening 36 and the at least one tack opening 38. In a non-limiting embodiment of the second portion 26, the at least one fastener opening 36 includes internal threads 82 that engage the fastener 96 (FIG. 12) to secure the fastener 96 to the compression plate 20. In another non-limiting embodiment of the second portion 26, the at least one fastener opening 36 is defined by a smooth internal surface.

The at least one tack opening 38 extends in a non-perpendicular direction relative to the outer surface 64 and the inner surface 66 such that an inlet on the outer surface 64 to each of the tack openings 38 is spaced closer to the second end 28 of the compression plate and an outlet to a corresponding tack opening 38 is spaced closer to the first end 24 of the compression plate 20. At least one of the inlet or the outlet to the tack opening 38 includes a chamfered edge 38a. The chamfered edge 38a extends a first distance along a passage of the tack opening 38 at a first edge portion closer to the first end 24 and a second distance along the passage at a second edge portion closer to the first second end 28. In one non-limiting embodiment, the first distance is greater than the second distance. In another non-limiting embodiment, the second distance is greater than the first distance. In yet another embodiment, the first distance is equal to the second distance.

Additionally, if there are multiple tack openings 38, the tack openings 38 could be staggered relative to each other along a length of the compression plate 20 such that a first tack opening is located closer to the first end 24 and a second tack opening is located closer to the second end 28. Alternatively, at least one tack opening 38 could be located distal of the at least one fastener opening 36 and adjacent the second end 28.

Figure 4A:
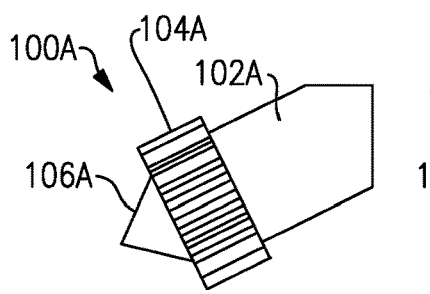
FIG. 4A illustrates a driver according to a first non-limiting embodiment of this disclosure.
Figure 4B:
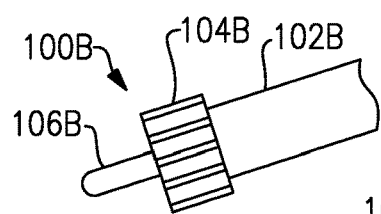
FIG. 4B illustrates a driver according to a second non-limiting embodiment of this disclosure.
Figure 4C:
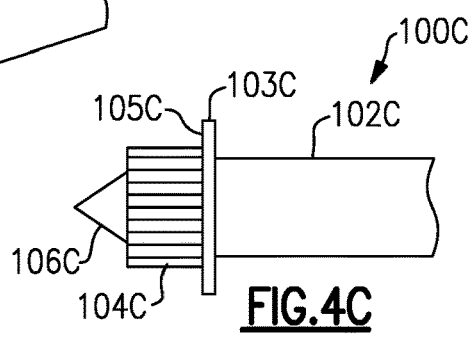
FIG. 4C illustrates a driver according to a third non-limiting embodiment of this disclosure.
Figure 4D:
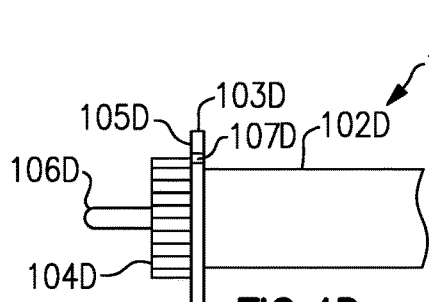
FIG. 4D illustrates a driver according to a fourth non-limiting embodiment of this disclosure.

Multiple different compression tools 100A-F can be used with the compression plate 20 as shown in FIGS. 4A-F. The compression tool 100A shown in FIG. 4A includes an elongated shaft 102A having a gear 104A located adjacent a pointed tip 106A on a distal end of the elongated shaft 102A. The compression tool 100B shown in FIG. 4B includes an elongated shaft 102B having a gear 104B located adjacent an elongated tip 106B having a rounded end. The compression tool 100C shown in FIG. 4C includes an elongated shaft 102C having a gear 104C located adjacent a pointed tip 106C on a distal end of the elongated shaft 102C and a shoulder 103C having a contact surface 105C for contacting the outer surface 64 of the compression plate 20 to prevent the compression tool 100C from passing through the compression plate 20. The compression tool 100D shown in FIG. 4D, is similar to the compression tool 100C but with an elongated tip 106D instead of the pointed tip 106C and an alignment mark 107D.

Figure 4E:
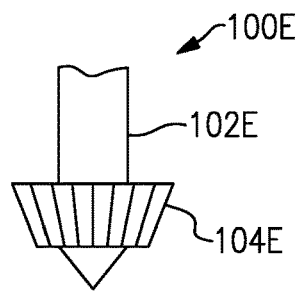
FIG. 4E illustrates a driver according to a fifth non-limiting embodiment of this disclosure.
Figure 4F:
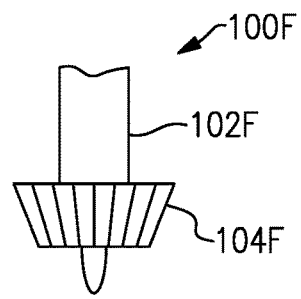
FIG. 4F illustrates a driver according to a sixth non-limiting embodiment of this disclosure.

The compression tools 100E-F shown in FIGS. 4E-F are similar to the compression tools 100A-B shown in FIGS. 4A-B, respectively, but the compression tools 100E-F include conical shaped gears 104E-F. The conical shaped gears 104E-F prevent the compression tools 100E-F from slipping past the compression plate 20 when inserted into the elongated slot 34. Additionally, when using the compression tools 100E-F, the teeth 68 on the compression plate 20 must have a slanted profile that corresponds to the conical shape of the conical gears 104E-F. Moreover, because the conical gears 104E-F taper towards tips 106E-F, respectively, the variation in tooth width on the conical gears 104E-F will maintain greater contact with the teeth 68 on the compression plate 20 if the compression plate 20 flexes or bends.

Although the tips 106A-F are shown having a specific shape, the tips 106A-F could be any other shape that contributes to fixing the compression tools 100A-F relative to bone.

Figure 5:
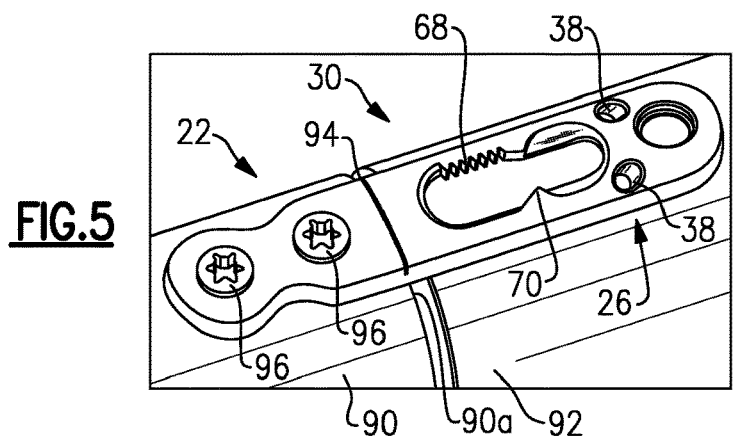
FIGS. 5-12 illustrate a non-limiting method of attaching adjacent bones utilizing the compression plate of FIG. 1.

An example method of using the compression plate 20 is illustrated in FIGS. 5-12. As shown in FIG. 5, the compression plate 20 connects a first bone 90 to a second bone 92. The first and second bones 90, 92 may be segments of the same bone or separate bones. The compression plate 20 is attached to the first bone 90 once an indicator 94 is aligned with an edge 90*a* of the first bone 90. In the illustrated non-limiting embodiment, the indicator 94 includes a line, such as a groove, a stripe, or a series of dots extending across the outer surface 64 of the compression plate 20. Alternatively, alphanumeric characters could be used as the indicator 94. By aligning the indicator 94 with the edge 90*a* of the first bone 90, a sufficient amount of the first bone 90 is present for the fasteners 96 to engage through the at least one fastener opening 32 to secure the compression plate 20 relative to the first bone 90.

Figure 6:
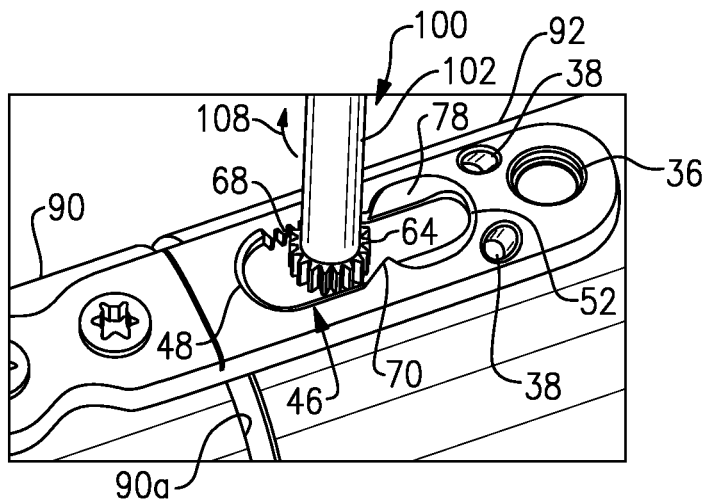

Once the fasteners 96 have secured the compression plate 20 to the first bone 90, one of the compression tools 100A-F is used to compress the first bone 90 and the second bone 92. The compression tool 100 is accepted within the elongated slot 34 adjacent the transition portion 70 such that the gear 104 is spaced from the first end 48 of the first slotted portion 46 of the elongated slot 34 as shown in FIG. 6. The tip 106 engages the second bone 92 to limit the amount of movement the tool 100 can make along a length of the second bone 92. When the compression tool 100B, 100D, or 100F is utilized, a hole is predrilled in the second bone 92 to accept the elongated tip 106B, 106D, 106F to prevent the tool 100B, 100D, 100F from moving longitudinally along the second bone 92. To compress the first and second bones 90, 92, the tool 100 is rotated in a clockwise direction 108 to engage the gear 104 on the tool 100 with the teeth 68 on the compression plate 20 to draw the second bone 92 towards the first bone 90. Alternatively, the tool 100 could also be located within the first slotted portion 46 closer to the first end 48 and rotated in a counterclockwise direction to achieve an opening wedge function and separate the first bone segment 90 and the second bone 92.

When an adequate or maximum amount of compression is applied to the first and second bones 90, 92 through the compression plate 20 and the tool 100, tacks 110 are used to temporarily secure the second portion 26 of the compression plate 20 to the second bone 92. If additional compression is required, the tool 100 could be relocated adjacent the transition portion 70 as discussed above and rotated clockwise to provide further compression once the tacks 110 are removed. The tacks 110 could then be reinserted into the compression plate 20 to temporarily secure the second portion 26 of the compression plate 20 to the second bone 92.

Figure 7:
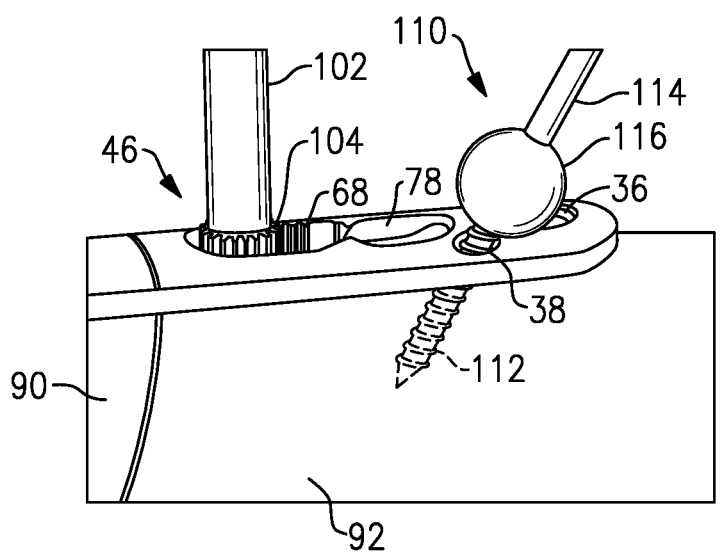
Figure 8:
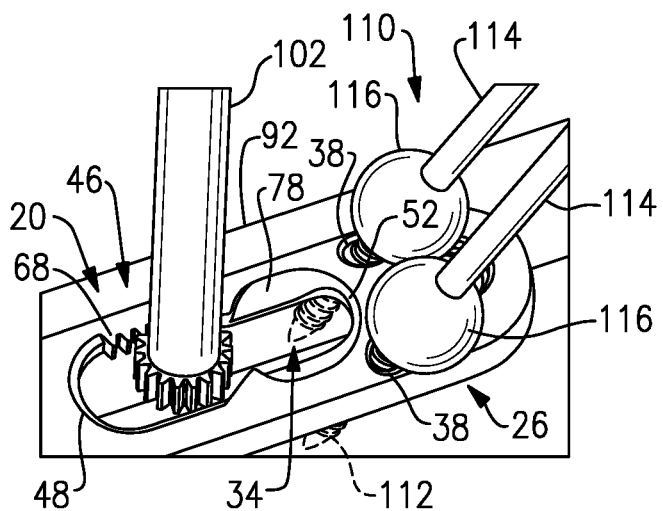

As shown in FIGS. 7 and 8, the tacks 110 includes a threaded end 112 separated from an elongated shaft 114 by a body 116, such as a spherical body or a body having a shoulder. The body 116 restricts the depth of penetration into the second bone 92 of the threaded end 112. The body 116 is sized to allow the tacks 110 to be accepted in each of the tack openings 38 without contacting each other and interfering with the placement of adjacent tacks 110. Additionally, when the tacks 110 are inserted into the tack openings 38, the tack 110 contributes to additional compression between the first and second bone 90, 92. The compression is the result of the body 116 of the tack 110 contacting the second edge portion closer the second end 28 and moving towards the first edge portion closer to the first end 24 and driving the second bone 92 towards the first bone 90 when the first distance of the first edge portion is greater than a second distance of the second edge portion.

Figure 9:
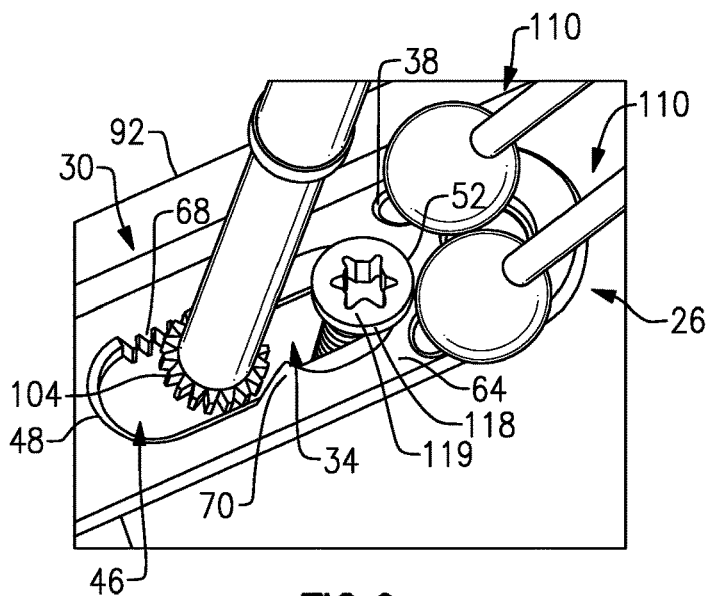
Figure 10:
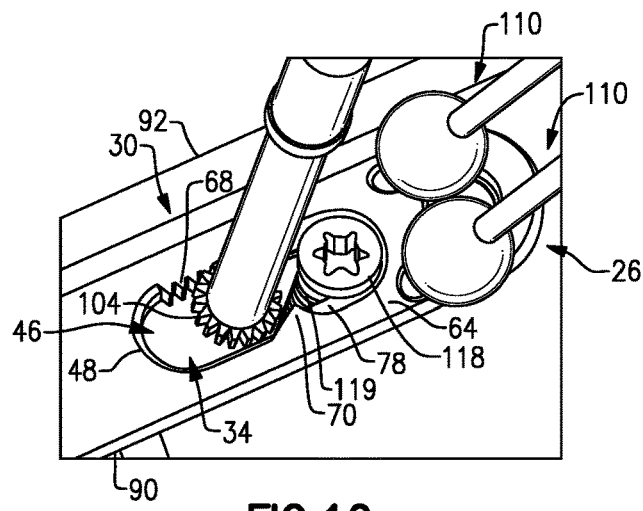

As shown in FIGS. 8-9, the tacks 110 remain in the tack openings 38 while a hole is drilled through the second bone 92 adjacent the second end 52 of the second slotted portion 50 of the elongated slot 34. A fastener 118 is accepted within the hole drilled in the second bone 92 such that the fastener 118 is located adjacent the second end 52. A head 119 of the fastener 118 at least partially engages the outer surface 64 of the compression plate 20 as shown in FIG. 10.

Figure 11:
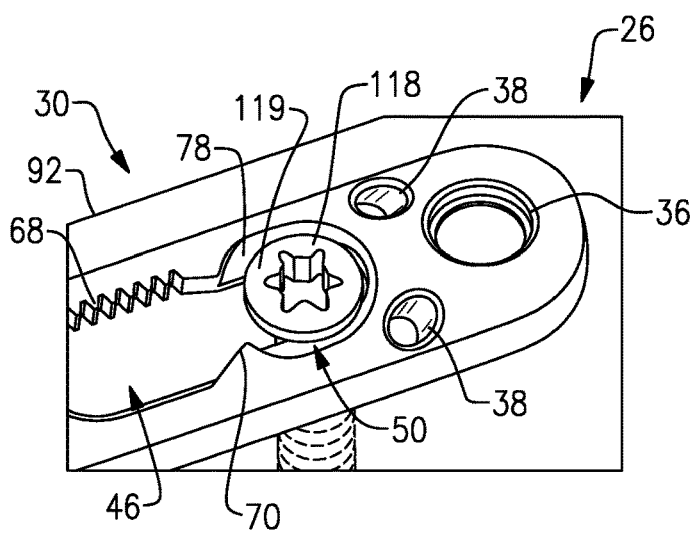

During the final stages of tightening the fastener 118, the tacks 110 are removed from the compression plate 20 as shown in FIG. 11. The variation in the ramped portion 78 between the second dimension D2 and the first dimension D1 provides additional compression between the first and second bones 90, 92. The additional compression occurs when the fastener 118 slides down the ramped portion 78 as the head 119 of the fastener 118 is brought into closer proximity with the second bone 92. This pushes the second bone 92 toward the first bone 90 as the fastener 118 moves through the elongated slot 34 from the second end 52 towards the first end 48 due to the variation in dimension of the surface portion 81. Unlike the fastener 96, the fastener 118 does not threadably engage the compression plate 20 to allow the fastener 118 to slide longitudinally through the second slotted portion 50 of the elongated slot 34.

Once the fastener 118 is secured, one or more fasteners 96 will extend through the at least one fastener opening 36 to further secure the compression plate 20 to the second bone 92. The fastener 96 in the fastener opening 36 prevents the fastener 118 from sliding through the elongated slot 34 and reducing the compression between the first and second bones 90, 92 after installation.

Figure 13:
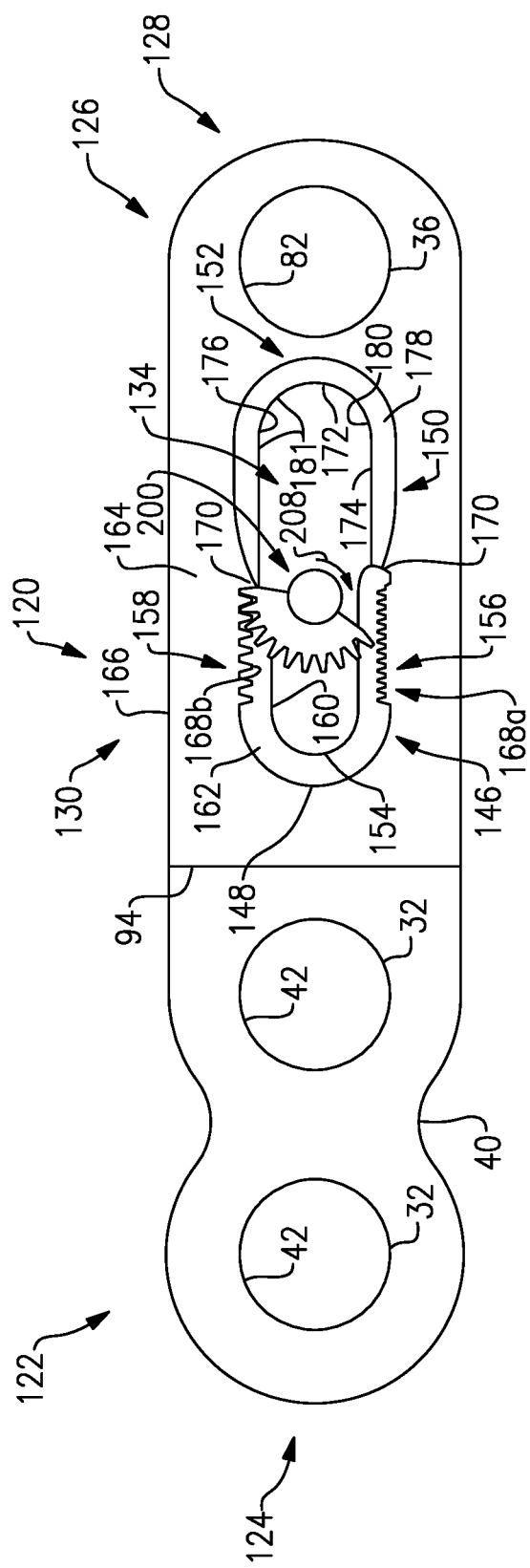
FIG. 13 illustrates a compression plate according to a second non-limiting embodiment of this disclosure.

FIG. 13 illustrate a second non-limiting embodiment of a compression plate 120 that is similar to the compression plate 20 shown in FIG. 1 except as otherwise described below or shown in the Figures.

The compression plate 120 is elongated and includes a first portion 122 adjacent a first end 124, a second portion 126 adjacent a second end 128, and a mid-portion 130 between the first portion 122 and the second portion 126. The first portion 122 includes at least one fastener opening 32, the mid-portion 130 includes an elongated slot 134, and the second portion 126 includes the at least one fastener opening 36. Although tack openings 38 are not shown in the illustrated non-limiting embodiment in FIG. 13, tack openings 38 could be incorporated into the compression plate 120. In one non-limiting embodiment, the compression plate 120 includes a longitudinal axis extending through the first end 124 and the second end 128 that is generally parallel to a length of the elongated slot 134.

The elongated slot 134 includes a first slotted portion 146 adjacent a first end 148 and a second slotted portion 150 adjacent a second end 152. The first end 148 of the elongated slot 134 is located closer to the first end 124 of the compression plate 120 than the second end 152 of the elongated slot 134 and the second end 152 of the elongated slot 134 is located closer to the second end 128 of the compression plate 120 than the first end 148 of the elongated slot 134. However, the location of the first end 148 and the second end 152 of the elongated slot 134 can vary in relation to the first end 124 and the second end 128 of the compression plate 120.

The first slotted portion 146 of the elongated slot 34 includes a first rounded portion 154 connecting a first side 156 of the elongated slot 134 to a second side 158 of the elongated slot 134. The first rounded portion 154 and the first and second sides 156 and 158 include a wall 160 having a chamfered portion 162. The wall 160 extends between an inner surface 166 of the compression plate and an outer surface 164 of the compression plate 120. The chamfered portion 162 is located adjacent the outer surface 164 of the compression plate 120 such that an edge of the chamfered portion 162 intersects the outer surface 164.

The first side 156 of the elongated slot 134 includes a first plurality of teeth 168a located on top of the chamfered portion 162 and adjacent the outer surface 164. In another non-limiting embodiment, the teeth 168a extend between the inner surface 166 and the outer surface 164. The first plurality of teeth 168a extend between a transition portion 170 along the chamfered portion 162 to the first rounded portion 154. The first plurality of teeth 168a include a first coarseness having a first density of teeth per unit length.

The second side 158 of the elongated slot 134 includes a second plurality of teeth 168b located on top of the chamfered portion 162 and adjacent the outer surface 164. In another non-limiting embodiment, the teeth 168b extend between the inner surface 166 and the outer surface 164. The second plurality of teeth 168b extend from the transition portion 170 along the chamfered portion 162 towards the first rounded portion 154. The second plurality of teeth 168b include a second coarseness having a second density of teeth per unit length with the first density of the first plurality of teeth 168a being greater than the second density of the second plurality of teeth 168b. Although the illustrated non-limiting embodiment shows the second plurality of teeth 168b extending from the outer surface 164 to the chamfered portion 162, the second plurality of teeth 168b could be positioned at the wall 160 such that the second plurality of teeth 168b extend between the inner surface 166 and the outer surface 164. Additionally, the first density of the first plurality of teeth 168a could be greater than, less than, or equal to the second density of the second plurality of teeth 168b.

The transition portions 170 separate the first slotted portion 146 from the second slotted portion 150 while still allowing the elongated slot 134 to extending between the first slotted portion 146 and the second slotted portion 150.

The second slotted portion 150 of the elongated slot 134 includes a second rounded portion 172 connecting a first side 174 of the second slotted portion 150 with a second side 176 of the second slotted portion 150. The first and second sides 174, 176 and the second rounded portion 172 each include a ramped portion 178, such as a chamfer or transition surface. The ramped portion 178 forms a surface for engaging a screw head.

The first and second sides 174, 176 and the second rounded portion 172 for a wall 180. The wall 180 includes a surface portion 181 and the ramped portion 178, such as a chamfer or another transition surface. The surface portion 181 extends from the inner surface 166 and intersects the ramped portion 178. The intersection between the ramped portion 178 and the surface portion 181 tapers toward the inner surface 166 from the second rounded portion 172 towards the transition portions 170. The ramped portion 178 also forms a contact surface for engaging a screw head to provide compression between separated bones as discussed further below.

The compression plate 120 connects the first bone 90 and the second bone 92 with a similar method as shown in FIGS. 5-12 except as otherwise described below or shown in the Figures.

Figure 14A:
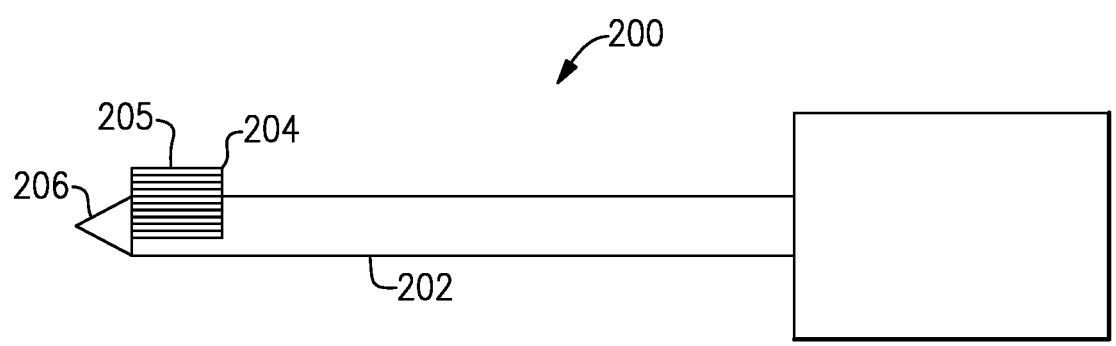
FIG. 14A illustrates a driver according to a seventh non-limiting embodiment of this disclosure.
Figure 14B:
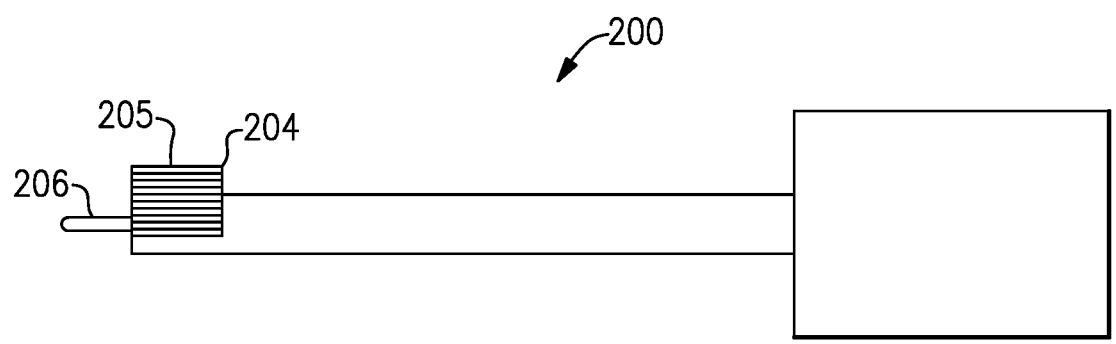
FIG. 14B illustrates a driver according to an eighth non-limiting embodiment of this disclosure.

Once the first portion 122 of the compression plate 120 is connected to the first bone 90 as described above, a tool 200 is used to compression the first bone 90 and the second bone 92. As shown in FIG. 14A, the compression tool 200 includes an elongated shaft 202 having a gear 204 located adjacent a tip 206 on the distal end of the elongated shaft 202. Similarly, as shown in FIG. 14B, the compression tool 200' includes the elongated shaft 202 having the gear 204 located adjacent an elongated tip 206' on the distal end of the elongated shaft 202. Alternatively, the tip 206 could be any other shape that contributes to fixing the compression tool 200 relative to bone. The gear 204 includes a plurality of teeth 205 that extend in a direction generally parallel to the elongated shaft 202. As shown in FIGS. 13 and 14, the gear 204 extends around the shaft less than 360 degrees. In the illustrated non-limiting embodiment, the gear 204 extends less than 180 degrees around the elongated shaft 202.

The compression tool 200 is accepted within the elongated slot 134 adjacent the transition portion 170 such that the gear 204 is spaced from the first end 148 of the first slotted portion 146 of the elongated slot 134 as shown in FIG. 13. The tip 206 engages the second bone 92 to limit the amount of movement the tool 200 can make along a length of the second bone 92. To compress the first and second bones 90, 92, the tool 200 is rotated in a clockwise direction 208 to engage the gear 204 on the tool 200 with the second plurality of teeth 168b in the elongated slot 134 to draw the second bone 92 towards the first bone 90.

As the tool 200 is rotated in the clockwise direction 208, the teeth on the gear 204 get progressively closer to the first plurality of teeth 168a. While the second plurality of teeth 168b serve the primary purpose of contributing to the compressive force being applied to the first and second bones 90, 92, the first plurality of teeth 168a provide a locking function with the tool 200. The locking function of the first plurality of teeth 168a restricts the tool 200 from rotating in the counterclockwise direction once a locking portion, such as a portion of the teeth 205 on the gear 204, has engaged the first plurality of teeth 168a. The coarseness of the first plurality of teeth 168a can be adjusted to a desired density to provide adequate adjustability in locking the tool 200 from rotating. Additionally, the depth of the first plurality of teeth 168a and/or a dimensional tolerance between the tool 200 and the compression plate 120 may be controlled to provide even further adjustability in locking the tool 200 from rotating. The tooth depth and dimensional tolerance allow the teeth 205 on the gear 204 to slip past adjacent peaks of the first plurality of teeth 168a before establishing a meshing engagement with the first plurality of teeth 168a while securely maintaining the teeth 205 in meshing engagement with the second plurality of teeth 168b during rotation.

When adequate compression is applied to the first and second bones 90, 92 through the compression plate 120 and the tool 200, the locking function of the tool 200 maintains compression between the first and second bones 90, 92. When the tool 200' is used in place of the tool 200, a hole is predrilled into the second bone 92 to accept the elongated tip 206'. Then a hole is drilled through the second bone 92 adjacent the second end 152 of the second slotted portion 150 of the elongated slot 134. The fastener 118 is accepted within the drilled hole adjacent the second slotted portion 150 of the elongated slot 134. The head 119 of the fastener 118 at least partially engages the outer surface 164 of the compression plate 120.

During the final stages of tightening the fastener 118, the tool 200 can be removed. The variation in the ramped portion 178 in the second slotted portion 150 of the elongated slot 134 provides additional compression between the first and second bones 90, 92. The additional compression occurs when the fastener 118 slides down the ramped portion 178 as the head 119 of the fastener 118 is brought into closer proximity with the second bone 92. This pushes the second bone 92 toward the first bone 90 as the fastener 118 moves through the elongated slot 134 from the second end 152 towards the first end 148 due to the variation in dimension of the wall 180.

Once the fastener 118 is secured, at least one additional fastener 96 extends through the at least one fastener opening 36 to further secure the compression plate 120 to the second bone 92. The fastener 96 in the at least one fastener opening 36 prevents the fastener 118 from sliding through the elongated slot 134 and reducing the compression between the first and second bones 90, 92.

Figure 15:
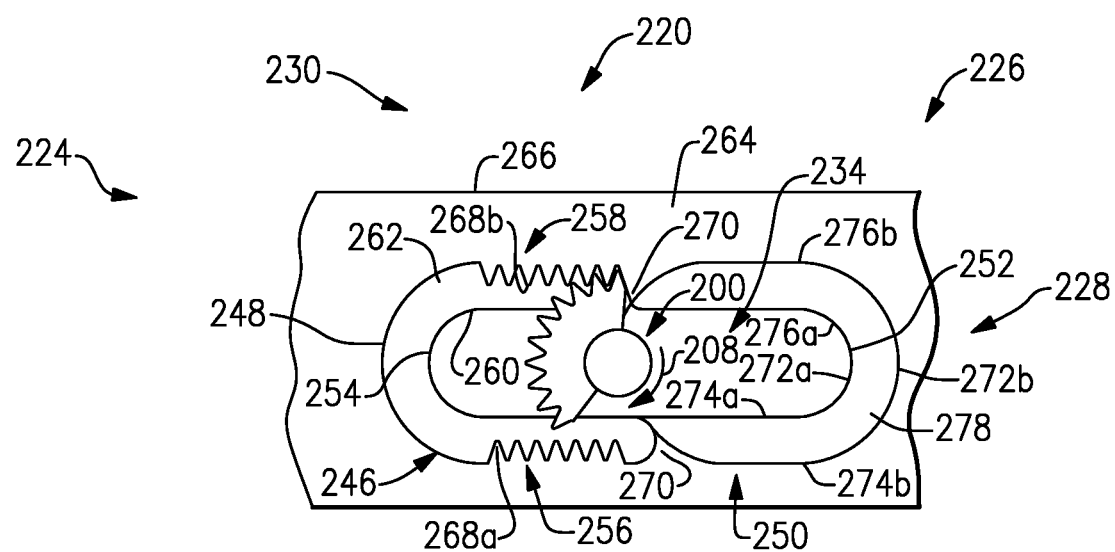
FIG. 15 illustrates a portion of a compression plate according to a third non-limiting embodiment of this disclosure.

FIG. 15 illustrate a mid-portion 230 according to a third non-limiting embodiment of a compression plate 220 that is similar to the mid-portions 30, 130 shown in FIGS. 1 and 13 except as otherwise described below or shown in the Figures.

The mid-portion 230 includes an elongated slot 234 includes a first slotted portion 246 adjacent a first end 248 and a second slotted portion 250 adjacent a second end 252. The first end 248 of the elongated slot 234 is adjacent a first end 224 of the compression plate 220 and the second end 252 of the elongated slot 234 is adjacent a second end 228 of the compression plate 220.

The first slotted portion 246 of the elongated slot 234 includes a first rounded portion 254 connecting a first side 256 of the elongated slot 234 to a second side 258 of the elongated slot 234. The first rounded portion 254 and the first and second sides 256 and 258 include a wall 260 having a chamfered portion 262. The wall 260 extends between an inner surface 266 of the compression plate 220 and an outer surface 264 of the compression plate 220. The chamfered portion 262 is located adjacent the outer surface 264 of the compression plate 220 such that an edge of the chamfered portion 262 intersects the outer surface 264.

The first side 256 of the elongated slot 234 includes a first plurality of teeth 268a located on top of the chamfered portion 262 and adjacent the outer surface 264. In another non-limiting embodiment, the teeth 268a extend between the inner surface 266 and the outer surface 264. The first plurality of teeth 268a extend between a transition portion 270 along the chamfered portion 262 to the first rounded portion 254. The first plurality of teeth 268a include a first coarseness having a first density of teeth per unit length. Although the illustrated non-limiting embodiment shows the first plurality of teeth 268a extending from the outer surface 264 to the chamfered portion 262, the first plurality of teeth 268a could be positioned at the wall 260 such that the first plurality of teeth 268a extend between the inner surface 266 and the outer surface 264.

The second side 258 of the elongated slot 234 includes a second plurality of teeth 268b located on top of the chamfered portion 262 and adjacent the outer surface 264. In another non-limiting embodiment, the teeth 268b extend between the inner surface 266 and the outer surface 264. The second plurality of teeth 268b extend from the transition portion 270 along the chamfered portion 262 towards the first rounded portion 254. The second plurality of teeth 268b include a second coarseness having a second density of teeth per unit length with the first density of the first plurality of teeth 268a being greater than the second density of the second plurality of teeth 268b. Although the illustrated non-limiting embodiment shows the second plurality of teeth 268b extending from the outer surface 264 to the chamfered portion 262, the second plurality of teeth 268b could be positioned at the wall 260 such that the second plurality of teeth 168b extend between the inner surface 266 and the outer surface 264.

Additionally, the first density of the first plurality of teeth 268a could be greater than, less than, or equal to the second density of the second plurality of teeth 268b.

The transition portions 270 separate the first slotted portion 246 from the second slotted portion 250 will still allowing the elongated slot 234 to extending between the first slotted portion 246 and the second slotted portion 250.

The second slotted portion 250 of the elongated slot 234 includes a second inner rounded portion 272a connecting a first inner side 274a of the second slotted portion 250 with a second inner side 276a of the second slotted portion 250. A ledge 278 forms a ledge between the second inner rounded portion 272a, the first inner side 274a, and the second inner side 276a and a second outer rounded portion 272b, a first outer side 274b, and a second outer side 276b, respectively. The second outer rounded portion 272b, the first outer side 274b, and the second outer side 276b extend between the ledge 278 and the outer surface 264. The ledge 278 forms a surface for engaging a screw head.

A method of connecting the first bone 90 and the second bone 92 with the compression plate 220 utilizes a similar method as shown in FIGS. 5-12 and described in relation to FIGS. 13 and 14.

When adequate compression is applied to the first and second bones 90, 92 through the compression plate 220 and the tool 200, the locking function of the tool 200 maintains compression between the first and second bones 90, 92. Then a hole is drilled through the second bone 92 adjacent the second end 252 of the second slotted portion 250 of the elongated slot 234. The fastener 118 is accepted within the drilled hole adjacent the second slotted portion 250 of the elongated slot 234. The head 119 of the fastener 118 (see FIG. 13) engages the ledge 278 allowing the fastener 118 to slide through the second slotted portion 250 without providing additional compression between the first and second bones 90, 92 during the final states of tightening the fastener 118.

As discussed above in relation to the compression plates 20 and 120, once the fastener 118 is secured in the second slotted portion 250, at least one fastener 96 extends through the at least one fastener opening 36 to further secure the compression plate 220 to the second bone 92. The fastener 96 in the at least one fastener opening 36 prevents the fastener 118 from sliding along the ledge 278 and reducing the compression between the first and second bones 90, 92.

Figure 16:
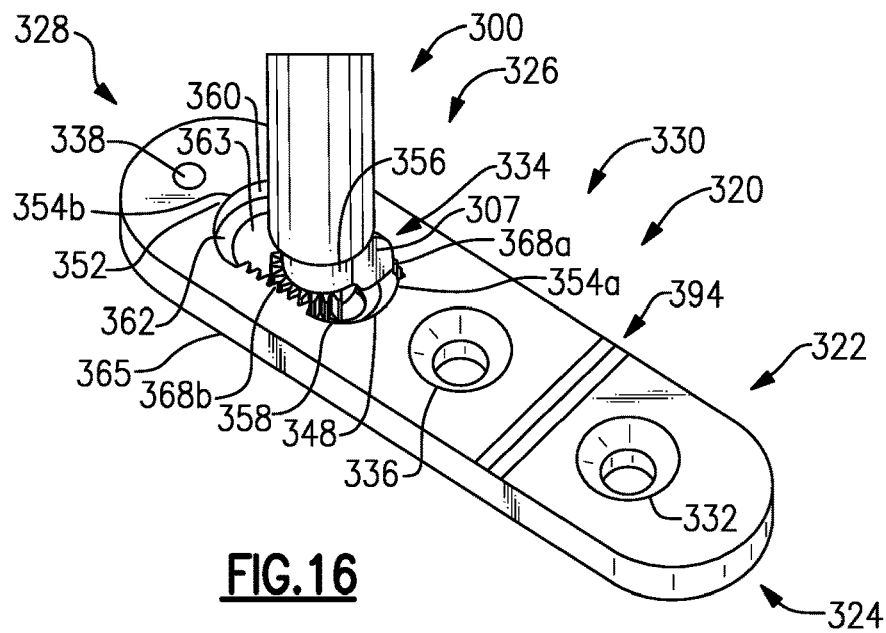
FIG. 16 illustrates a compression plate according to a fourth non-limiting embodiment of this disclosure.

FIG. 16 illustrate a fourth non-limiting embodiment of a compression plate 320 and tool 300 that are similar to the compression plate 120 and tool 100, respectively, except as otherwise described below or shown in the Figures.

The compression plate 320 is elongated and includes a first portion 322 adjacent a first end 324, and a second portion 326 adjacent a second end 328, and a mid-portion 330 between the first portion 322 and the second portion 324. The first portion 322 includes at least one fastener opening 332, the second portion 326 includes an elongated slot 334 and at least one tack opening 338, and the mid-portion 330 includes at least one fastener opening 336 and an indicator 394. In one non-limiting embodiment, the compression plate 320 includes a longitudinal axis extending through the first end 324 and the second end 328 that is generally parallel to a length of the elongated slot 334.

The elongated slot 334 includes a first end 348 and a second end 352. The first end 348 of the elongated slot 334 is located closer to the first end 324 of the compression plate 320 than the second end 352 of the elongated slot 334 and the second end 352 of the elongated slot 334 is located closer to the second end 328 of the compression plate 320 than the first end 348 of the elongated slot 334. However, the location of the first end 348 and the second end 352 of the elongated slot 334 can vary in relation to the first end 324 and the second end 328 of the compression plate 320.

The elongated slot 334 includes a first rounded portion 354a and a second rounded portion 354b connecting a first side 356 of the elongated slot 334 to a second side 358 of the elongated slot 334. The first and second rounded portions 354a, 354b and the first and second sides 356, 358 include an outer wall 360 extending between an outer surface 364 and an inner ledge 362. A chamfer 363 extends between an inner wall 365 and the inner ledge 362. The inner wall 365 is located adjacent an inner surface 366 of the compression plate 320.

The first side 356 of the elongated slot 334 includes a first plurality of teeth 368a located on top of the inner ledge 362 and adjacent the outer surface 364. In a non-limiting embodiment, the first plurality of teeth 368a follow a curved path such that a distance from the first plurality of teeth 368a to the chamfer 363 varies between the first and second rounded portions 354a, 354b. In another non-limiting embodiment, the teeth 368a extend between the inner surface 366 and the outer surface 364. The first plurality of teeth 368a extend between the first and second rounded portions 354a and 354b. The first plurality of teeth 368a include a first coarseness having a first density of teeth per unit length.

The second side 358 of the elongated slot 334 includes a second plurality of teeth 368b located on top of the inner ledge 362 and adjacent the outer surface 364. The second plurality of teeth 368b extend between the first and second rounded portions 354a, 354b. The second plurality of teeth 368b include a second coarseness having a second density of teeth per unit length with the first density of the first plurality of teeth 368a being greater than the second density of the second plurality of teeth 368b. Alternatively, the first density of the first plurality of teeth 368a could be greater than, less than, or equal to the second density of the second plurality of teeth 368b.

Although the illustrated non-limiting embodiment shows the second plurality of teeth 368b extending from the outer surface 364 to the inner ledge 362, the second plurality of teeth 368b could be positioned at the inner wall 365 such that the second plurality of teeth 368b extend between the inner surface 366 and the outer surface 364.

The compression plate 320 connects the first bone 90 and the second bone 92 with a similar method as shown in FIGS. 5-12 and discussed above except as otherwise described below or shown in the Figures.

Figure 17:
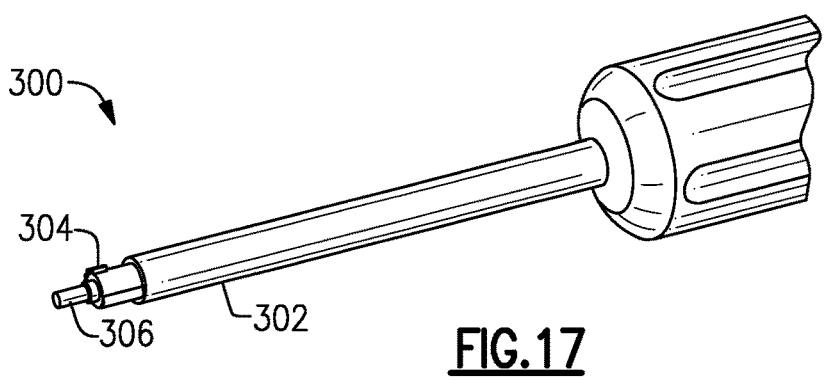
FIG. 17 illustrates a driver according to a ninth non-limiting embodiment of this disclosure.
Figure 18:
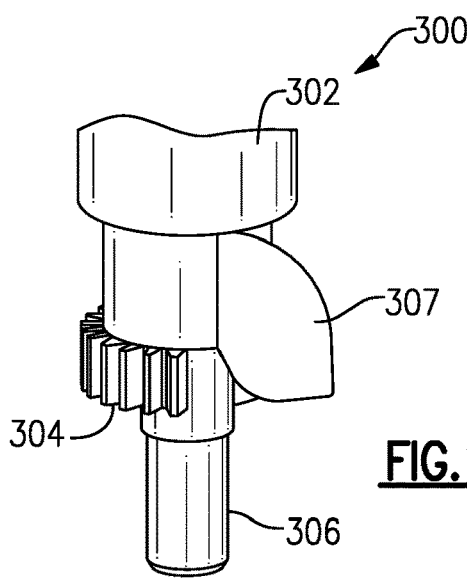
FIG. 18 illustrates an enlarged view of an end portion of the driver of FIG. 17.

Once the first portion 322 of the compression plate 320 is connected to the first bone 90 using a method similar to the method described above, a tool 300 is used to compression the first bone 90 and the second bone 92. As shown in FIGS. 17-18, the compression tool 300 includes an elongated shaft 302 with a gear 304 located adjacent an elongated tip 306 on the distal end of the elongated shaft 302, and a locking portion, such as a spring pawl 307, located adjacent gear 304 and the elongated shaft 302.

In a non-limiting embodiment of the tool 300, the elongated tip 306 could include a pointed tip for piecing the second bone 92. In a non-limiting embodiment of the spring pawl 307, the spring pawl 307 is made of a metallic or composite material that wraps around a portion of the elongated shaft 302 with a first end 307a located in a slot 305 on the elongated shaft 302 and a second end 307b for engaging the first plurality of teeth 368a. As shown in FIG. 18, the second end 307b includes a curved portion that is at least partially axially aligned with the gear 304 relative to a longitudinal axis of the elongated shaft 302.

Figure 19:
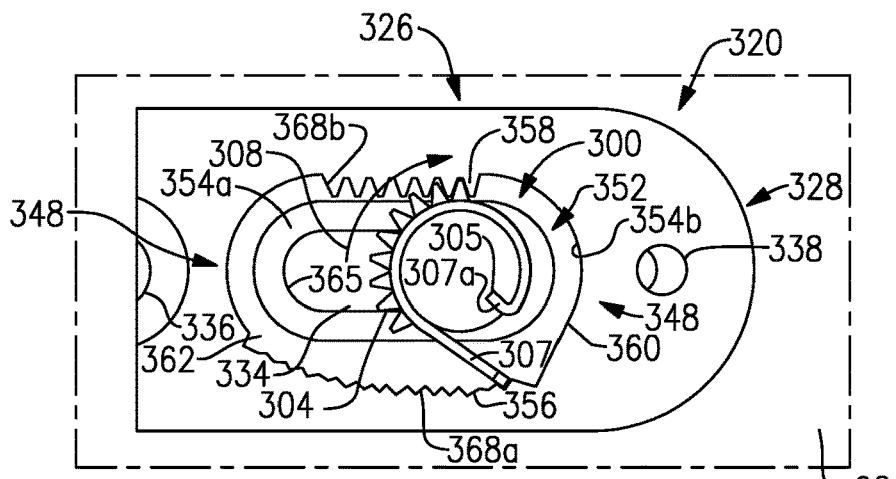
FIGS. 19-21 illustrate a method of attaching adjacent bones according to another non-limiting embodiment of this disclosure.

As shown in FIG. 19, the compression tool 300 is accepted within the elongated slot 334 adjacent the second end 352 of the elongated slot 334. The elongated tip 306 is accepted within a predrilled hole in the bone 92 located adjacent the second end 352 of the elongated slot 334. The elongated tip 306 engages the predrilled hole in the second bone 92 to limit the amount of movement the tool 300 can make along a length of the second bone 92. To compress the first and second bones 90, 92, the tool 300 is rotated in a clockwise direction 308 to engage the spring pawl 307 on the tool 300 with the first plurality of teeth 368a in the elongated slot 334 to draw the second bone 92 towards the first bone 90.

Figure 20:
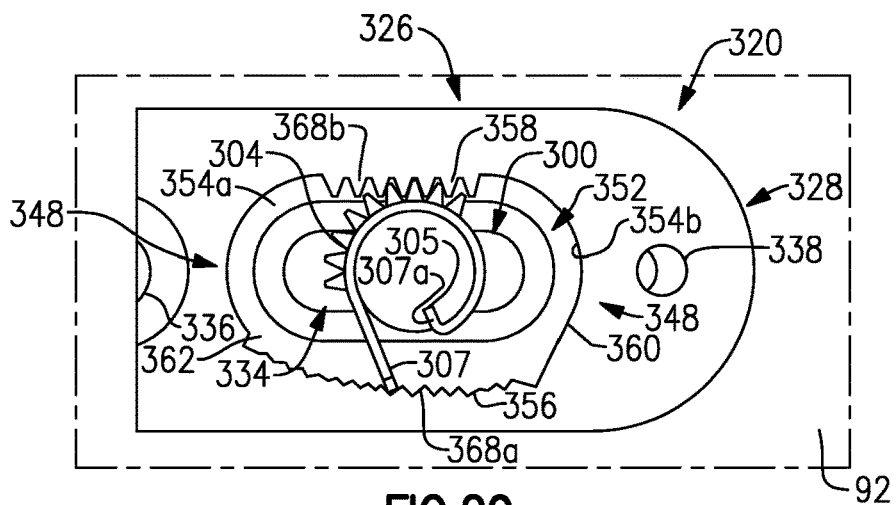
Figure 21:
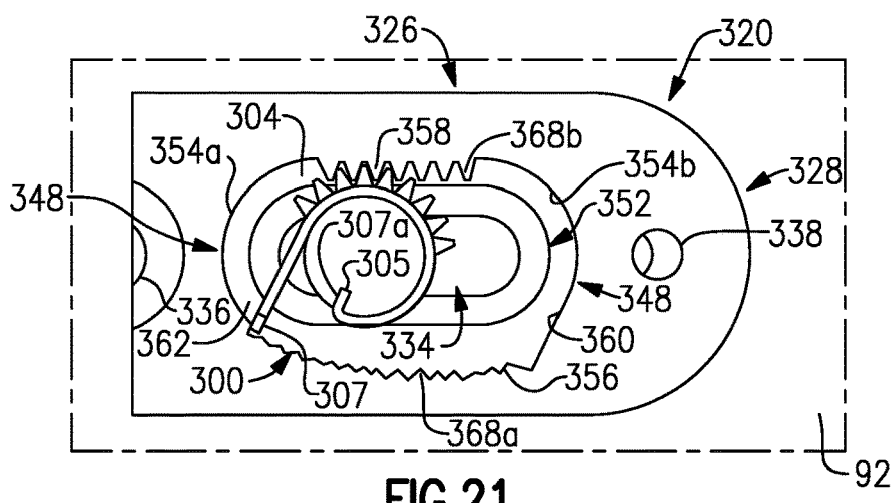

As the tool 300 is rotated in the clockwise direction 308, the second end 307b of the spring pawl 307 get progressively closer to the first rounded portion 354a as shown in FIGS. 19-21. While the second plurality of teeth 368b serve the primary purpose of contributing to the compressive force being applied to the first and second bones 90, 92, the first plurality of teeth 368a provide a locking function with the tool 300. The locking function of the first plurality of teeth 368a restricts the tool 300 from rotating in the counterclockwise direction. The coarseness of the first plurality of teeth 368a can be adjusted to a desired density to provide adequate adjustability in locking the tool 300 from rotating.

When adequate compression is applied to the first and second bones 90, 92 through the compression plate 320 and the tool 300, the locking function of the tool 200 maintains compression between the first and second bones 90, 92. Additionally, the tack 110 may be placed through the tack opening 338 to further limit movement of the first and second bones 90, 92 relative to each other. If more compression between the first and second bones 90, 92 is needed, the tool 300 could be removed from the compression plate 320 and inserted in a new predrilled hole in the second bone 92 adjacent the second end 352. Then a hole is drilled through the fastener opening 336 into the second bone 92. Once the fastener 96 in the fastener opening 336 has been tightened, the tool 300 and the tack 110 can be removed. Alternatively, an additional fastener 96 could be placed within the elongated slot 334.

Additionally, the compression plate 320 could include the ramped portion 78, 178 or ledge 278 shown in FIGS. 2, 13, and 15, respectively, and the tool 300 having the spring pawl 307 could be used with the compression plates 120 and 220.

Figure 22:
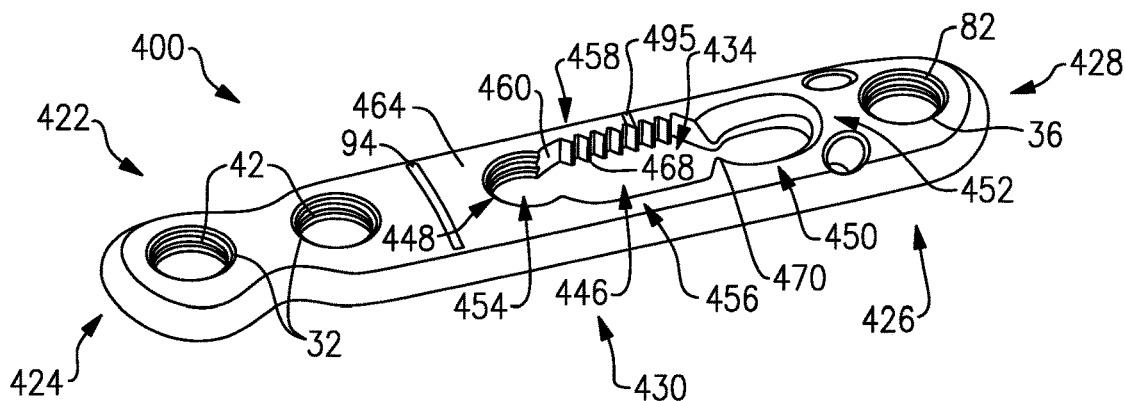
FIG. 22 illustrates a compression plate according to a fifth non-limiting embodiment of this disclosure.
Figure 23:
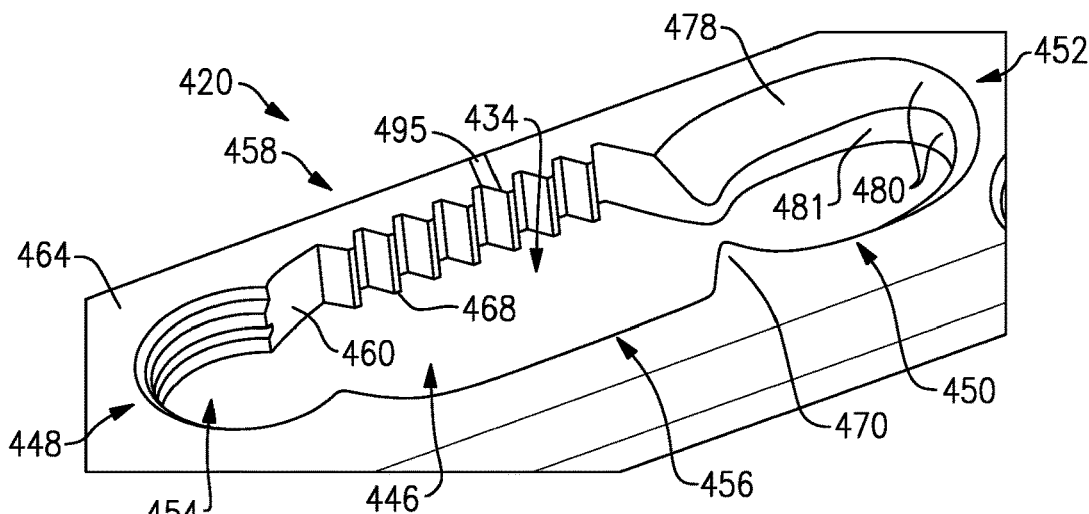
FIG. 23 illustrates an enlarged view of a portion of the compression plate shown in FIG. 22.
Figure 25:
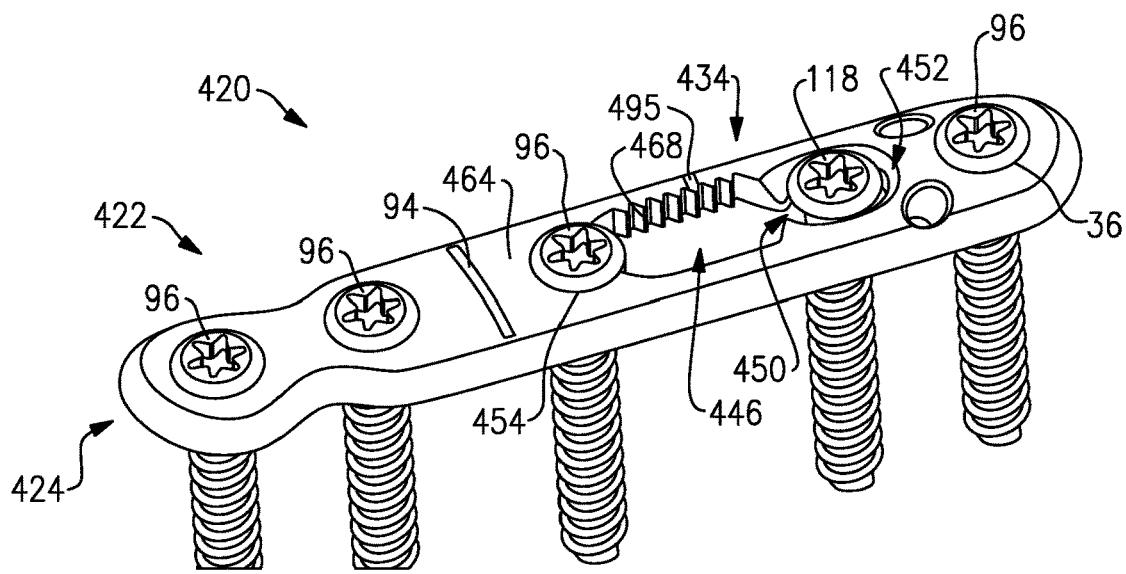
FIG. 25 illustrates the compression plate of FIG. 22 with a plurality of fasteners.
Figure 24:
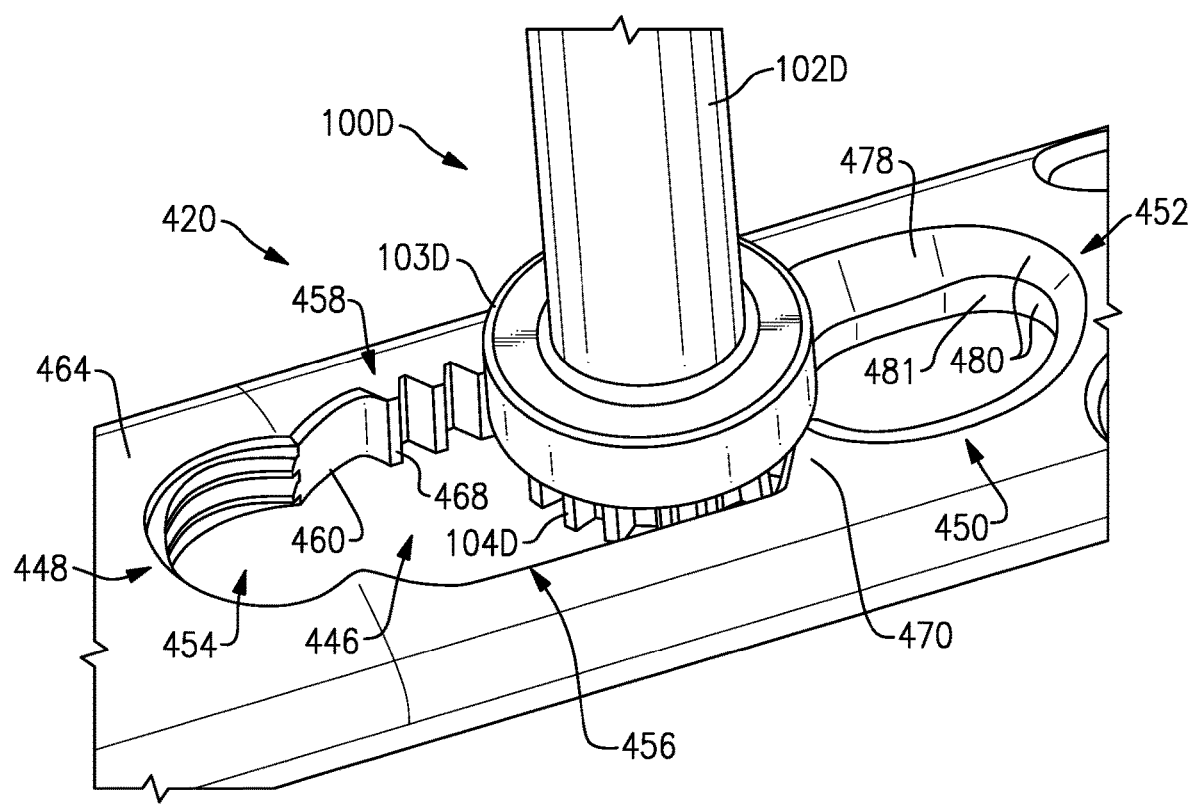
FIG. 24 illustrates the driver shown in FIG. 4D with the compression plate of FIG. 22.

FIG. 22 illustrates a fifth non-limiting embodiment of a compression plate 420 that is similar to the compression plate 20 shown in FIG. 1 except as otherwise described below or shown in the Figures.

The compression plate 420 is elongated and includes a first portion 422 adjacent a first end 424, a second portion 426 adjacent a second end 428, and a mid-portion 430 between the first portion 422 and the second portion 424.

The first portion 422 includes at least one fastener opening 32, the mid-portion 430 includes an elongated slot 434, and the second portion 126 includes the at least one fastener opening 36. In one non-limiting embodiment, the compression plate 420 includes a longitudinal axis extending through the first end 424 and the second end 428 that is generally parallel to a length of the elongated slot 434.

The elongated slot 434 includes a first slotted portion 446 adjacent a first end 448 and a second portion 450 adjacent a second end 452. The first end 448 of the elongated slot 434 is located closer to the first end 424 of the compression plate 420 than the second end 452 of the elongated slot 434 and the second end 452 of the elongated slot 434 is located closer to the second end 428 of the compression plate 420 than the first end 448 of the elongated slot 434. However, the location of the first end 448 and the second end 452 of the elongated slot 434 can vary in relation to the first end 424 and the second end 428 of the compression plate 420.

The first slotted portion 446 of the elongated slot 434 includes a threaded fastener opening 454 connecting and extending between a first side 456 of the elongated slot 434 to a second side 458 of the elongated slot 434. The elongated slot 434 is also at least partially defined by a wall 460. The threaded fastener opening 454 is also only partially defined by the wall 460 such that the threaded fastener opening 454 is open into the elongated slot 434 and includes a sidewall extending less than 360 degrees.

The second side 458 of the elongated slot 434 includes a plurality of teeth 468 extending from the wall 460 between an outer surface 464 and an inner surface 466. The plurality of teeth 468 extend from a transition portion 470 along the wall 460 towards the threaded fastener opening 454.

The transition portions 470 separates the first slotted portion 446 from the second slotted portion 450 while still allowing the elongated slot 434 to extending between the first slotted portion 446 and the second slotted portion 450. The second slotted portion 450 of the elongated slot 434 is similar to the second slotted portion 450 of the compression plate 120 shown in FIG. 13 except where shown in the Figures.

The compression plate 420 connects the first bone 90 and the second bone 92 with a similar method as shown in FIGS. 5-12 except as otherwise described below or shown in the Figures. Moreover, similar components between the compression plate 420 and the compression plate 20 will include a leading 4 unless otherwise noted.

Once the first portion 422 of the compression plate 420 is connected to the first bone 90 as described with respect to the above embodiments, one of the tools 100A-F, such as the tool 100D, is used to compress the first bone 90 and the second bone 92 by engaging the gear 104D with the teeth 468. The compression plate 420 includes an alignment mark 495 that aligns with the alignment mark 107D on the tool 100D to ensure proper placement of the tool 100D. A fastener 118 provides travels along the second slotted portion 450 to provide additional compression between the first bone and the second bone 92 as the fastener 118 is tightened. The first and second bones 92 are further locked from movement after the dynamic compression from the fastener 118 by the fasteners 96 in the fastener opening 36 and the threaded fastener opening 454. Because the proximity of the fastener 96 in the threaded fastener opening 454 to the separation between the first bone 90 and the second bone 92, the fastener 96 in the threaded fastener opening 454 will maximize the bending strength of the compression plate 420.

Although the different non-limiting embodiments are illustrated as having specific components, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should also be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claim should be studied to determine the true scope and content of this disclosure.

What is claimed is:

1. A bone plate comprising:
   a body portion;
   a first slotted portion extending at least partially through the body portion;
   a plurality of teeth adjacent the first slotted portion for engaging a driver in the first slotted portion;
   a second slotted portion extending at least partially through the body portion, wherein the first slotted portion and the second slotted portion are connected by a transition opening such that the first slotted portion and the second slotted portion form one continuous slot; and
   a ramped portion at least partially surrounding the second slotted portion, the ramped portion tapering from an outer surface of the body portion toward an inner surface of the body portion.

2. The bone plate of claim 1, wherein the body portion includes a first end and a second end, wherein the first end includes at least one fastener opening for attaching the body portion to a first bone segment and wherein the second slotted portion is configured to align with a second bone segment separate from the first bone segment.

3. The bone plate of claim 2, wherein the plurality of teeth are located on a first side of the first slotted portion and a second plurality of teeth are located on a second side of the first slotted portion.

4. The bone plate of claim 1, wherein the second slotted portion includes a wall including the ramped portion and a surface portion,
   wherein the ramped portion extends from an intersection with the outer surface of the body portion to an intersection with the surface portion.

5. The bone plate of claim 4, wherein the surface portion includes a first dimension extending perpendicular from an intersection with the inner surface of the body portion to the ramped portion along a first side of the second slotted portion and wherein the surface portion includes a second dimension extending perpendicular from the inner surface of the body portion to the ramped portion at a second end of the second slotted portion with the second dimension being greater than the first dimension.

6. The bone plate of claim 5, wherein an intersection between the ramped portion and the surface portion tapers toward the inner surface in a direction from the second end of the second slotted portion to a first end of the second slotted portion.

7. The bone plate of claim 6, wherein the first end of second slotted portion is configured to be closer to a first bone segment than the second end of the second slotted portion.

8. The bone plate of claim 1, wherein the first slotted portion includes a threaded fastener opening and the threaded fastener opening includes a sidewall extending less than 360 degrees.

9. The bone plate of claim 1, wherein the body portion is a single piece unitary component.

10. The bone plate of claim 1, wherein the inner surface at least partially surrounds both the first slotted portion and the second slotted portion and the inner surface defines a bone contact surface.

11. The bone plate of claim 1, wherein the inner surface defines a bone contact surface and the outer surface is located on an opposite side of the body portion from the inner surface.

12. A bone plate assembly comprising:
a bone plate including a body portion;
a driver;
a first slotted portion extending at least partially through the body portion;
a first plurality of teeth adjacent a first side of the first slotted portion for engaging the driver in the first slotted portion; and
a second plurality of teeth adjacent a second side of the first slotted portion for engaging the driver in the first slotted portion, wherein the first plurality of teeth include a first coarseness and the second plurality of teeth include a second coarseness different from the first coarseness, and wherein the second plurality of teeth engage a locking portion of the driver.

13. The assembly of claim 12, further comprising a second slotted portion extending at least partially through the body portion and a ramped portion at least partially surrounding the second slotted portion, wherein the ramped portion tapers from an outer surface of the body portion toward an inner surface of the body portion.

14. The assembly of claim 13, wherein the second slotted portion includes a wall having the ramped portion and a surface portion and the ramped portion extends from an intersection with the outer surface of the body portion to an intersection with the surface portion, wherein the surface portion includes a first dimension extending perpendicular from an intersection with the inner surface of the body portion to the ramped portion along a first side of the second slotted portion and wherein the surface portion includes a second dimension extending perpendicular from the inner surface of the body portion to the ramped portion at a second end of the second slotted portion with the second dimension being greater than the first dimension.

15. The assembly of claim 14, wherein an intersection between the ramped portion and the surface portion tapers toward the inner surface in a direction from the second end of the second slotted portion to a first end of the second slotted portion.

16. The assembly of claim 12, wherein the driver includes a gear for engaging the first plurality of teeth and the locking portion for engaging the second plurality of teeth.

17. The assembly of claim 16, wherein the locking portion includes a spring pawl at least partially surrounding a portion of the driver and the spring pawl includes a first end located in a slot in the driver and second end for engaging the second plurality of teeth.

18. The bone plate assembly of claim 12, wherein the driver includes an elongated shaft with a handle located at a proximal end of the elongated shaft, a tip located at a distal end of the elongated shaft, and a gear located adjacent the tip for engaging the first plurality of teeth.

19. A bone plate comprising:
a body portion including a first end and a second end, wherein the first end includes at least one fastener opening for attaching the body portion to a first bone segment;
a first slotted portion extending at least partially through the body portion;
a plurality of teeth adjacent the first slotted portion for engaging a driver in the first slotted portion, wherein the plurality of teeth are located on a first side of the first slotted portion and a second plurality of teeth are located on a second side of the first slotted portion;
a second slotted portion extending at least partially through the body portion, wherein the second slotted portion is configured to align with a second bone segment separate from the first bone segment; and
a ramped portion at least partially surrounding the second slotted portion, the ramped portion tapering from an outer surface of the body portion toward an inner surface of the body portion;
wherein the plurality of teeth include a first coarseness having a first density of teeth per unit length and the second plurality of teeth include a second coarseness having a second density of teeth per the unit of length different, wherein the second coarseness is different from the first coarseness, and wherein the second plurality of teeth engage a locking portion of the driver.

* * * * *